United States Patent [19]
Hoskins et al.

[11] Patent Number: 5,821,335
[45] Date of Patent: Oct. 13, 1998

[54] **BIOSYNTHETIC GENE MURG FROM *STREPTOCOCCUS PNEUMONIAE***

[75] Inventors: Jo Ann Hoskins; Paul Luther Skatrud, both of Indianapolis; Robert Brown Peery, Brownsburg, all of Ind.

[73] Assignee: Eli Lilly and Company, Indianapolis, Ind.

[21] Appl. No.: 751,474

[22] Filed: Nov. 19, 1996

[51] Int. Cl.$^6$ .................. C07K 14/315; G01N 33/53; A61K 39/09
[52] U.S. Cl. .................. 530/350; 530/300; 530/388.4; 435/7.1; 435/7.34; 435/15; 435/32; 435/36; 435/69.1; 424/234.1; 424/244.1
[58] Field of Search .................... 435/7.1, 7.34, 435/15, 32, 36, 69.1; 530/350, 300, 388.4; 424/234.1, 244.1

[56] References Cited

U.S. PATENT DOCUMENTS 5,501,957  3/1996  Denny et al. .
5,525,616  6/1996  Platt et al. .

OTHER PUBLICATIONS

Dominique Mengin–Lecreulx, et al., *Journal of Bacteriology*, Aug. 1991, pp. 4625–2636.

*Primary Examiner*—Paula K. Hutzell
*Assistant Examiner*—Khalid Masood
*Attorney, Agent, or Firm*—Thomas D. Webster; David E. Boone

[57] ABSTRACT

The invention provides isolated nucleic acid compounds encoding the stem peptide biosynthetic gene murG of *Streptococcus pneumoniae*. Also provided are vectors and transformed heterologous host cells for expressing the MurG enzyme product and a method for identifying compounds that inhibit stem peptide biosynthesis.

3 Claims, 1 Drawing Sheet

BIOSYNTHETIC GENE MURG FROM STREPTOCOCCUS PNEUMONIAE

BACKGROUND OF THE INVENTION

This invention relates to recombinant DNA technology. In particular the invention pertains to the cloning of the murG gene encoding undecaprenyl-PP-MurNAc-pentapeptideGlcNAc transferase of *Streptococcus pneumoniae* and the use of the murG gene and the encoded protein in a screen for new inhibitors of bacterial cell wall biosynthesis.

The emergence of antibiotic resistance in common pathogenic bacterial species has justifiably alarmed the medical and research communities. Frequently these organisms are co-resistant to several different antibacterial agents. Pathogens resistant to frequently utilized antibiotics are found in the clinical as well as the community setting. Particularly problematic in the community setting has been the emergence and rapid spread of beta-lactam resistance in *Streptococcus pneumoniae* which frequently causes upper respiratory tract infections. Resistance to beta-lactams in this organism is due to modification of one or more of the penicillin-binding proteins (PBP's) which are involved in cell wall biosynthesis and are the targets for beta-lactam antibiotics.

Interference with bacterial cell wall biosynthesis is an especially attractive antibacterial target because an analogous structure does not exist in mammalian cells so that compounds that interfere with cell wall biosynthesis have low toxicity in humans and potentially high therapeutic value.

The bacterial cell wall structure contains a peptidoglycan layer which provides mechanical rigidity for the bacterium. This segment of the cell wall is composed of a sugar backbone (alternating residues of N-acetylglucosamine and N-acetylmuramic acid) attached to a pentapeptide (also referred to as "stem peptide," or "Park nucleotide") containing alternating D and L amino acid residues. The nascent peptidoglycan layer is stabilized by an enzymatic step which crosslinks adjacent pentapeptide moieties. Without this crosslinking step the peptidoglycan structure is severely weakened and susceptible to degradation. Indeed, it is the peptidoglycan crosslinking step that has been a frequently targeted site for antibiotic compounds such as the beta-lactam antibiotics.

Unlike the peptidoglycan crosslinking step, the stem peptide pathway has not been widely exploited as a target for inhibitory compounds. The stem peptide biosynthetic pathway comprises at least 10 steps in which the stem peptide is added onto UDPMurNAc by the stepwise addition of amino acid residues. In the first step, catalyzed by the UDPGlcNAc enolpyruvyl transferase and NADH-dependent reductase, UDPGlcNAc is converted to UDPMurNAc. In five subsequent steps, catalyzed by UDP-N-acetylmuramate:L-alanine ligase; UDP-N-acetyl-muramyl-L-alanine:D-glutamate ligase; UDP-N-acetyl-muramyl-L-alanyl-D-isoglutamate:L-lysine ligase; UDP-N-acetylmuramyl-L-alanyl-D-isoglutamyl-L-lysine:D-alanyl-D-alanine ligase; and D-alanyl-D-alanine ligase, the final product, UDPMurNAc-L-Ala-D-isoGlu-L-lysine-D-Ala-D-Ala, is produced in *Streptococcus pneumoniae*.

The enzymatic steps involved in the formation of the stem peptide are potential targets for new antibacterial agents. A few inhibitors, which target this pathway, have been developed. For example, D-cycloserine inhibits alanine racemase and D-alanine-D-alanine ligase; phosphonomycin inhibits the conversion of UDP-GlcNAc to UDP-GlcNac-enolpyruvate; and Alafosfalin inhibits the formation of UDP-MurNac-L-Ala.

While inroads in the development of new antibiotics and new targets for antibiotic compounds have emerged in a variety of microorganisms, progress has been less apparent in *Streptococcus pneumoniae*. In part, *Streptococcus pneumoniae* presents a special case because this organism is highly mutagenic and readily takes up and integrates exogenous foreign DNA from its surroundings, thereby increasing the possibility of creating novel genes. Thus, the need for new antibacterial compounds and new targets for antibacterial therapy is especially acute in *Streptococcus pneumoniae*.

SUMMARY OF THE INVENTION

The present invention is designed to meet the aforementioned need and provides, inter alia, isolated nucleic acid molecules that encode the murG gene product from *Streptococcus pneumoniae*. The invention also provides the protein product of the *Streptococcus pneumoniae* murG gene, undecaprenyl-PP-MurNAc-pentapeptideGlcNAc transferase (MurG protein), in substantially purified form.

Having the cloned murG gene of *Streptococcus pneumoniae* enables the production of recombinant MurG protein and the implementation of large scale screens to identify new inhibitory compounds targeted at the stem peptide biosynthetic pathway. It may be possible to combine stem peptide proteins in a single screen to examine several steps at the same time. Structural analysis of the MurG protein will enable structure-based drug design to develop novel compounds effective in the treatment of antibiotic resistant microorganisms.

In one embodiment the present invention relates to an isolated DNA molecule encoding MurG protein, said DNA molecule comprising the nucleotide sequence identified as SEQ ID NO. 1:

In another embodiment the present invention relates to a MurG protein molecule, wherein said protein molecule comprises the sequence identified as SEQ ID NO. 2.

In a further embodiment the present invention relates to a ribonucleic acid molecule encoding MurG protein, said ribonucleic acid molecule comprising the sequence identified as SEQ ID NO. 3:

In yet another embodiment, the present invention relates to a recombinant DNA vector which incorporates the *Streptococcus pneumoniae* murG gene in operable linkage to gene expression sequences enabling the murG gene to be transcribed and translated in a host cell.

In still another embodiment the present invention relates to homologous or heterologous host cells which have been transformed or transfected with the cloned murG gene of *Streptococcus pneumoniae* such that the murG gene is expressed in the host cell.

In a still further embodiment, the present invention relates to a method for identifying compounds that inhibit the enzymatic activity of the MurG protein of *Streptococcus pneumoniae*.

DEFINITIONS

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"MurG" refers to the protein encoded by murG, undecaprenyl-PP-MurNAc-pentapeptideGlcNAc transferase.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by temperature and salt concentration.

DETAILED DESCRIPTION

The murG gene of *Streptococcus pneumoniae* encodes the stem peptide pathway enzyme undecaprenyl-PP-MurNAc-pentapeptideGlcNAc transferase (SEQ ID NO.2). The stem peptide pathway is necessary for the synthesis of the peptidoglycan layer, which is part of the bacterial cell wall. There are at least 10 steps involved in stem peptide biosynthesis.

The murG gene of *Streptococcus pneumoniae* comprises a DNA sequence of 1059 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

Gene Isolation Procedures

Those skilled in the art will recogize that the murG gene may be obtained by a plurality of applicable genetic and recombinant DNA techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the murG gene of *Streptococcus pneumoniae* or fragment thereof could be isolated by PCR amplification of *Streptococcus pneumoniae* genomic DNA or cDNA using oligonucleotide primers targeted to any suitable region of SEQ ID NO. 1. Methods for PCR amplification are widely known in the art. See e.g. *PCR Protocols: A Guide to Method and Application,* Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One embodiment of the present invention relates to the substantially purified protein encoded by the murG gene, or functionally related proteins of *Streptococcus pneumoniae*.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney,

*Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celsius or below, preferably −20° C. for thirty minutes followed by thirty minutes at 0° C.

The protein of the present invention can also be produced by recombinant DNA methods using the cloned murG gene of *Streptococcus pneumoniae*. Recombinant methods are preferred if a high yield is desired. Expression of the cloned murG gene can be carried out in a variety of suitable host cells well known to those skilled in the art. The murG gene is introduced into a host cell by any suitable means, for example transformation, transfection or electroporation, well known to those skilled in the art. While chromosomal integration of the cloned murG gene is within the scope of the present invention, it is preferred that the gene be cloned into a suitable extra-chromosomally maintained expression vector so that the coding region of the murG gene is operably linked to a constitutive or inducible promoter.

The basic steps in the recombinant production of the MurG protein are:

a) constructing a natural, synthetic or semi-synthetic DNA encoding MurG protein;

b) integrating said DNA into an expression vector in a manner suitable for expressing the MurG protein, either alone or as a fusion protein;

c) transforming or otherwise introducing said vector into an appropriate eucaryotic or procaryotic host cell forming a recombinant host cell, d) culturing said recombinant host cell in a manner to express the MurG protein; and e) recovering and substantially purifying the MurG protein by any suitable means, well known to those skilled in the art.

Expressing Recombinant MurG Protein in Procaryotic and Eucaryotic Host Cells

In general, procaryotes are used for cloning DNA sequences and for constructing the vectors of the present invention. Procaryotes may also be employed in the production of the MurG protein. For example, the *Escherichia coli* K12 strain 294 (ATCC No. 31446) is particularly useful for the procaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed as host cells in the cloning and expression of the recombinant proteins of this invention.

Promoter sequences suitable for driving the expression of genes in procaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to procaryotes, a variety of mammalian cell systems and eucaryotic microorganisms such as yeast are suitable host cells. The yeast *Saccharomyces cerevisiae* is the most commonly used eucaryotic microorganism. A number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1auxotrophic mutant.

Purification of Recombinantly-Produced MurG Protein

An expression vector carrying the cloned murG gene of *Streptococcus pneumoniae* is transformed or transfected into a suitable host cell using standard methods. Cells which contain the vector are then propagated under conditions suitable for expression of the MurG protein. If the gene is under the control of an inducible promoter then suitable growth conditions would incorporate the appropriate inducer. The recombinantly-produced protein may be purified from cellular extracts of transformed cells by any suitable means. In a preferred process for protein purification the murG gene is modified at the 5' end to incorporate several histidine residues at the amino terminus of the MurG protein product. This "histidine tag" enables a single-step protein purification method referred to as "immobilized metal ion affinity chromatography" (IMAC), essentially as described in U.S. Pat. No. 4,569,794 which hereby is incorporated by reference. The IMAC method enables rapid isolation of substantially pure MurG protein starting from a crude cellular extract.

Other embodiments of the present invention comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one codon due to the degeneracy of the genetic code. Because these alternative nucleic acid sequences would encode the same amino acid sequences, the present invention further comprises these alternate nucleic acid sequences.

The murG gene, which comprises nucleic acid encoding SEQ ID NO:2, may be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the murG gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

In an alternative methodology, namely PCR, the murG DNA sequence comprising a portion or all of SEQ ID NO:1 can be generated from *Streptococcus pneumoniae* genomic DNA using suitable oligonucleotide primers complementary to SEQ ID NO:1 or region therein, as described in U.S. Pat. No. 4,889,818, which hereby is incorporated by reference. Suitable protocols for performing the PCR are disclosed in, for example, *PCR Protocols: A Guide to Method and Applications,* Ed. Michael A. Innis et al., Academic Press, Inc. (1990).

The ribonucleic acids of the present invention may be prepared using the polynucleotide synthetic methods discussed supra, or they may be prepared enzymatically using RNA polymerase to transcribe a murG DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques including, for example, hybridization screens of genomic or subgenomic libraries. A nucleic acid compound comprising SEQ ID NO:1, SEQ ID NO:3 or a complementary sequence thereof, or a fragment thereof, and which is at least 18 base pairs in length, and which will selectively hybridize to *Streptococcus pneumoniae* DNA or mRNA encoding murG, is provided. Preferably, the 18 or more base pair compound is DNA. See e.g. B. Wallace and G. Miyada, "Oligonucleotide Probes for the Screening of Recombinant DNA Libraries," In *Methods in Enzymology,* Vol. 152, 432–442, Academic Press (1987).

The probes and primers of this invention can be prepared by enzymatic methods well known to those skilled in the art (See e.g. Sambrook et al. supra). In a most preferred embodiment the probes and primers are synthesized using chemical means as described above.

Another aspect of the present invention relates to recombinant DNA cloning vectors and expression vectors comprising the nucleic acids of the present invention. Some of the vectors encompassed by this invention are described above. The preferred nucleic acid vectors are those which comprise DNA. The most preferred recombinant DNA vectors comprise the isolated DNA sequence, SEQ ID NO:1. Plasmid pJAHmurG is an especially preferred DNA vector of the present invention.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. The skilled artisan will recognize a number of inducible promoters which respond to a variety of inducers, for example, carbon source, metal ions, heat, and others. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. A preferred host is *E. coli* which has been transfected or transformed with a vector which comprises a nucleic acid of the present invention.

Figure 1:
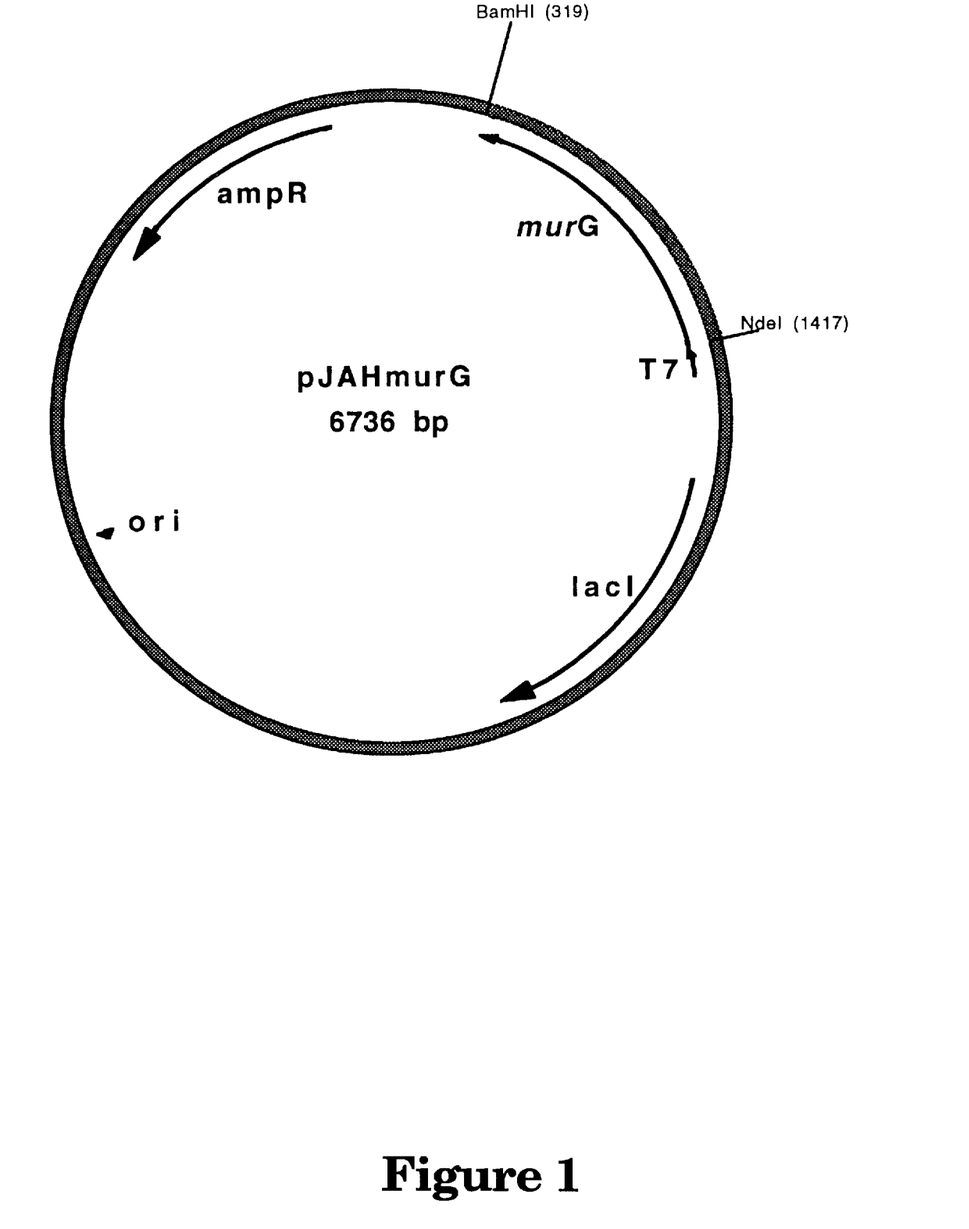
FIG. 1 Plasmid pJAHmurG, useful for high level expression of the *Streptococcus pneumoniae* murG gene in the heterologous procaryotic host cell *Eschericia coli*.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. The preferred host cell is any strain of *E. coli* which can accomodate high level expression of an exogenously introduced gene. Preferred vectors for expression are those which comprise SEQ ID NO:1. An especially preferred expression vector for use in *E. coli* is plasmid pJAHmurG, which comprises SEQ ID NO:1. (See FIGURE). Transformed host cells may be cultured under conditions well known to skilled artisans such that SEQ ID NO:2 is expressed, thereby producing MurG protein in the recombinant host cell.

For the purpose of identifying or developing inhibitors of the stem peptide pathway, it would be desirable to determine those agents which inhibit the MurG step. A method for determining whether a substance will inhibit the enzymatic reaction catalyzed by the MurG protein comprises contacting the MurG protein with a test inhibitory compound and monitoring MurG enzyme activity by any suitable means.

The instant invention provides such a screening system useful for discovering compounds which inhibit the MurG protein, said screening system comprising the steps of:

a) preparing MurG enzyme;

b) exposing said MurG enzyme to a test inhibitor;

c) introducing a specific MurG substrate; and d) quantifying by any suitable means the loss of activity of said MurG enzyme.

Utilization of the screening system described above provides a means to determine compounds which interfere with stem peptide biosynthesis. This screening method may be adapted to automated procedures such as a PANDEX® (Baxter-Dade Diagnostics) system, allowing for efficient high-volume screening of potential therapeutic agents.

In such a screening protocol MurG enzyme is prepared as described herein, preferably using recombinant DNA technology. A test inhibitory compound is then introduced into the reaction vessel containing the MurG enzyme, followed by addition of enzyme substrate. Alternatively, substrate may be added simultaneously with the test compound. For example, in a preferred method radioactively or chemically-labeled substrate may be used. The products of the enzymatic reaction are assayed for the chemical label or radioactivity by any suitable means. The absence or diminution of the chemical label or radioactivity in the product indicates the degree to which the reaction is inhibited.

Skilled artisans will recognize that $IC_{50}$ values are dependent on the selectivity of the compound tested. For example, a compound with an $IC_{50}$ which is less than 10 nM is generally considered an excellent candidate for drug therapy. However, a compound which has a lower affinity, but is selective for a particular target, may be an even better candidate. The skilled artisan will recognize that any information regarding inhibitory activity or selectivity of a particular compound is beneficial in the pharmaceutical arts.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Streptococcus pnuemoniae* murG Gene in a Heterologous Host Plasmid pJAHmurG (See FIGURE) is an approximately 6700 base pair expression vector suitable for expressing the murG gene of *S. pneumoniae* in the procaryotic host *E. coli*. This plasmid contains an origin of replication (Ori), an ampicillin resistance gene (Amp), useful for selecting cells which have incorporated the vector following a tranformation procedure, and further comprises the lacI gene for repression of the lac operon, as well as the T7 promoter and T7 terminator sequences in operable linkage to the coding region of the murG gene. Parent plasmid pET11A (obtained from Novogen, Madison, Wis.) is digested with endonucleases NdeI and BamHI. Linearized pET11A is ligated to a DNA fragment bearing NdeI and BamHI sticky ends and further comprising the coding region of the *S. pneumoniae* murG gene.

The murG gene ligated into pJAHmurG is prepared by PCR using suitable oligonucleotide primers which are complementary to the 5' and 3' ends of SEQ ID NO.1. The primers are constructed to contain BamHI and NdeI cloning sites. The murG gene is modified at the 5' end (amino terminus of encoded protein) in order to simplify purification of the encoded MurG protein product. For this purpose, the oligonucleotide used to prime the 5' end of the gene encodes 8 histidine residues and a factor Xa cleavage site inserted after the ATG start codon at nucleotide positions 1 to 3 of SEQ ID NO: 1. Placement of the histidine residues at the amino terminus of the encoded MurG protein serves to enable the IMAC one-step protein purification procedure (See below).

EXAMPLE 2

Expression of *Streptococcus pneumoniae* murG Gene in *Echerichia coli* and Purification of MurG Enzyme Plasmid pJAHmurG is transformed into *E. coli* BL21 (DE3) (hsdS gal λcIts857 ind1Sam7nin5lacUV5-T7gene 1) using standard methods (See e.g. Sambrook et al. Supra). Transformants, selected for resistance to ampicillin, are chosen at random and tested for the presence of pJAHmurG by agarose gel electrophoresis using quick plasmid preparations. Id. Colonies that contain pJAHmurG are grown, processed, and the protein product encoded by the murG gene purified by immobilized metal ion affinity chromatography (IMAC), essentially as described in U.S. Pat. No. 4,569,794, the entire contents of which is hereby incorporated by reference.

Briefly, the IMAC column is prepared as follows. A metal-free chelating resin (e.g. SEPHAROSE 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract prepared from a recombinant host transformed or transfected with plasmid pJAHmurG.

After washing the column with a suitable buffer, pH 7.5 to remove unbound proteins and other materials, the bound recombinant MurG protein is eluted in a buffer at pH 4.3, essentially as described in U.S. Pat. No. 4,569,794.

EXAMPLE 3

Biochemical Assay for Inhibitors of *Streptococcus pneumoniae* MurG Enzyme Product The activity of the MurG enzyme is assayed by monitoring the transfer of UDP-linked peptidoglycan precursors to membranes prepared from *S. pneumoniae* using standard methods (See e.g. Mengin-Lecreulx et al. J. Bacteriol. 173, 4625–4636, 1991). Briefly, the reaction contains in a final volume of 25 ul, 0.2M Tris-HCl, pH 7.5, 40 mM $MgCl_2$, 30 mM ATP, 5 uM UDP-MurNAc-L-Ala-D-Glu-L-Lys-D-[$^{14}$C] Ala-D-Ala (0.4 GBq per mmol), 0.5 mM UDP-GlcNAc, and cellular membranes containing approximately 90 ug of total protein. Reactions are incubated for 5 minutes to 60 minutes at 35° C. After incubation samples are placed in a boiling water bath for 2 minutes and applied to Whatman 3 MM filter paper. The reaction proceeds by subjecting the filter to descending chromatography for 16 hours in isobutyric acid-1M NH$_4$OH (5:3 vol/vol). Areas corresponding to peptidoglycan, UDP-MurNAc-pentapeptide, and lipid intermediates are cut out and assayed by scintillation counting.

Inhibition studies are carried out using the reaction conditions described in the preceding paragraph. Test inhibitory compounds are added to a final concentration of between 1 mM and 10 mM, and the percentage inhibition ascertained by comparison with a control in which no test inhibitor is present.

---

We claim:

1. A substantially pure MurG protein from *Streptococcus pneumoniae* having the amino acid sequence:

| Met | Lys | Lys | Ile | Val | Phe | Thr | Gly | Gly | Gly |
| 1 | | | | 5 | | | | | 10 |
| Thr | Val | Gly | His | Val | Thr | Leu | Asn | Leu | Leu |
| | | | | 15 | | | | | 20 |
| Leu | Met | Pro | Lys | Phe | Ile | Glu | Asp | Gly | Trp |
| | | | | 25 | | | | | 30 |
| Glu | Val | His | Tyr | Ile | Gly | Asp | Lys | Arg | Gly |
| | | | | 35 | | | | | 40 |
| Ile | Glu | His | Gln | Glu | Ile | Leu | Lys | Ser | Gly |
| | | | | 45 | | | | | 50 |
| Leu | Asp | Val | Thr | Phe | His | Ser | Ile | Ala | Thr |
| | | | | 55 | | | | | 60 |
| Gly | Lys | Leu | Arg | Arg | Tyr | Phe | Ser | Trp | Gln |
| | | | | 65 | | | | | 70 |
| Asn | Met | Leu | Asp | Val | Phe | Lys | Val | Gly | Trp |
| | | | | 75 | | | | | 80 |
| Gly | Ile | Val | Gln | Ser | Leu | Phe | Ile | Met | Leu |
| | | | | 85 | | | | | 90 |
| Arg | Leu | Arg | Pro | Gln | Thr | Leu | Phe | Ser | Lys |
| | | | | 95 | | | | | 100 |
| Gly | Gly | Phe | Val | Ser | Val | Pro | Pro | Val | Ile |
| | | | | 105 | | | | | 110 |
| Ala | Ala | Arg | Val | Ser | Gly | Val | Pro | Val | Phe |
| | | | | 115 | | | | | 120 |
| Ile | His | Glu | Ser | Asp | Leu | Ser | Met | Gly | Leu |
| | | | | 125 | | | | | 130 |
| Ala | Asn | Lys | Ile | Ala | Tyr | Lys | Phe | Ala | Thr |
| | | | | 135 | | | | | 140 |
| Lys | Met | Tyr | Ser | Thr | Phe | Glu | Gln | Ala | Ser |
| | | | | 145 | | | | | 150 |
| Ser | Leu | Ser | Lys | Val | Glu | His | Val | Gly | Ala |
| | | | | 155 | | | | | 160 |
| Val | Thr | Lys | Val | Ser | Asp | Gln | Lys | Asn | Pro |
| | | | | 165 | | | | | 170 |
| Glu | Pro | Asp | Glu | Leu | Val | Asp | Ile | Gln | Thr |
| | | | | 175 | | | | | 180 |
| His | Phe | Asn | His | Lys | Leu | Pro | Thr | Val | Leu |
| | | | | 185 | | | | | 190 |
| Phe | Val | Gly | Gly | Ser | Ala | Gly | Ala | Arg | Val |
| | | | | 195 | | | | | 200 |
| Phe | Asn | Gln | Leu | Val | Thr | Asp | His | Lys | Lys |
| | | | | 205 | | | | | 210 |
| Glu | Leu | Thr | Glu | Arg | Tyr | Asn | Ile | Ile | Asn |
| | | | | 215 | | | | | 220 |
| Leu | Thr | Gly | Asp | Ser | Ser | Leu | Asn | Glu | Leu |
| | | | | 225 | | | | | 230 |
| Ser | Gln | Asn | Leu | Phe | Arg | Val | Asp | Tyr | Val |
| | | | | 235 | | | | | 240 |
| Thr | Asp | Leu | Tyr | Gln | Pro | Leu | Met | Glu | Leu |
| | | | | 245 | | | | | 250 |
| Ala | Asp | Val | Val | Val | Thr | Arg | Gly | Gly | Ala |
| | | | | 255 | | | | | 260 |
| Asn | Thr | Ile | Phe | Glu | Leu | Leu | Ala | Ile | Ala |
| | | | | 265 | | | | | 270 |
| Lys | Leu | His | Val | Ile | Val | Pro | Leu | Gly | Arg |
| | | | | 275 | | | | | 280 |
| Glu | Ala | Ser | Arg | Gly | Asp | Gln | Ile | Glu | Asn |
| | | | | 285 | | | | | 290 |
| Ala | Ala | Tyr | Phe | Val | Lys | Lys | Gly | Tyr | Ala |
| | | | | 295 | | | | | 300 |
| Glu | Asp | Leu | Gln | Glu | Ser | Asp | Leu | Thr | Leu |
| | | | | 305 | | | | | 310 |
| Asp | Ser | Leu | Glu | Glu | Lys | Leu | Ser | His | Leu |
| | | | | 315 | | | | | 320 |
| Leu | Ser | His | Lys | Glu | Asp | Tyr | Gln | Ala | Lys |
| | | | | 325 | | | | | 330 |
| Met | Lys | Ala | Ser | Lys | Glu | Leu | Lys | Ser | Leu |
| | | | | 335 | | | | | 340 |
| Ala | Asp | Phe | Tyr | Gln | Leu | Leu | Lys | Lys | Asp |
| | | | | 345 | | | | | 350 |
| Leu | Ser | | | | | | | | | which is SEQ ID NO 2.

2. A method for identifying inhibitory compounds of *Streptococcus pneumoniae* MurG protein activity of SEQ ID NO:2, comprising the steps of:

a) admixing in a suitable reaction buffer
        i) substantially pure MurG protein;
        ii) a suitable substrate;
        iii) a test inhibitory compound;
    b) measuring an amount of product formed; and
    c) comparing the amount of product formed at step (b) with a control reaction, said control reaction comprising steps (a)(i), (a)(ii), and (b); and wherein said control reaction lacks said test inhibitory compound.

3. A kit useful for identifying inhibitors of stem peptide biosynthesis said kit comprising:

a) substantially pure MurG protein; as depicted in SEQ ID NO:2 and
    b) a suitable substrate for said protein.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1059 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( i x ) FEATURE:
        ( A ) NAME/KEY: CDS
        ( B ) LOCATION: 1..1059

( x i ) SEQUENCE DESCRIPTION: SEQ ID NO:1:

| ATG | AAA | AAA | ATT | GTC | TTT | ACA | GGT | GGG | GGG | ACG | GTT | GGA | CAC | GTT | ACC | 48 |
|---|---|---|---|---|---|---|---|---|---|---|---|---|---|---|---|---|
| Met | Lys | Lys | Ile | Val | Phe | Thr | Gly | Gly | Gly | Thr | Val | Gly | His | Val | Thr | |
| 1 | | | | 5 | | | | | 10 | | | | | 15 | | |
| CTC | AAT | CTT | TTG | TTA | ATG | CCC | AAG | TTC | ATC | GAA | GAT | GGT | TGG | GAA | GTC | 96 |
| Leu | Asn | Leu | Leu | Leu | Met | Pro | Lys | Phe | Ile | Glu | Asp | Gly | Trp | Glu | Val | |
| | | | | 20 | | | | 25 | | | | | 30 | | | |
| CAC | TAT | ATC | GGG | GAC | AAG | CGT | GGT | ATC | GAA | CAC | CAA | GAA | ATC | CTT | AAG | 144 |
| His | Tyr | Ile | Gly | Asp | Lys | Arg | Gly | Ile | Glu | His | Gln | Glu | Ile | Leu | Lys | |
| | | 35 | | | | | 40 | | | | | 45 | | | | |
| TCA | GGT | TTG | GAT | GTC | ACT | TTC | CAC | TCC | ATT | GCG | ACT | GGG | AAA | TTG | CGT | 192 |
| Ser | Gly | Leu | Asp | Val | Thr | Phe | His | Ser | Ile | Ala | Thr | Gly | Lys | Leu | Arg | |
| | 50 | | | | | 55 | | | | | 60 | | | | | |
| CGC | TAT | TTC | TCT | TGG | CAA | AAT | ATG | CTG | GAC | GTC | TTC | AAA | GTT | GGC | TGG | 240 |
| Arg | Tyr | Phe | Ser | Trp | Gln | Asn | Met | Leu | Asp | Val | Phe | Lys | Val | Gly | Trp | |
| 65 | | | | | 70 | | | | | 75 | | | | | 80 | |
| GGA | ATC | GTC | CAA | TCG | CTC | TTT | ATC | ATG | TTG | CGA | CTT | CGT | CCA | CAG | ACC | 288 |
| Gly | Ile | Val | Gln | Ser | Leu | Phe | Ile | Met | Leu | Arg | Leu | Arg | Pro | Gln | Thr | |
| | | | | 85 | | | | | 90 | | | | | 95 | | |
| CTT | TTT | TCA | AAG | GGG | GGC | TTT | GTC | TCA | GTA | CCG | CCT | GTT | ATC | GCA | GCG | 336 |
| Leu | Phe | Ser | Lys | Gly | Gly | Phe | Val | Ser | Val | Pro | Pro | Val | Ile | Ala | Ala | |
| | | | 100 | | | | | 105 | | | | | 110 | | | |
| CGT | GTG | TCA | GGA | GTG | CCT | GTC | TTT | ATT | CAC | GAA | TCT | GAC | CTG | TCT | ATG | 384 |
| Arg | Val | Ser | Gly | Val | Pro | Val | Phe | Ile | His | Glu | Ser | Asp | Leu | Ser | Met | |
| | | 115 | | | | | 120 | | | | | 125 | | | | |
| GGC | TTG | GCC | AAT | AAA | ATC | GCC | TAT | AAA | TTT | GCG | ACT | AAG | ATG | TAT | TCA | 432 |
| Gly | Leu | Ala | Asn | Lys | Ile | Ala | Tyr | Lys | Phe | Ala | Thr | Lys | Met | Tyr | Ser | |
| | | 130 | | | | 135 | | | | | 140 | | | | | |
| ACC | TTT | GAG | CAA | GCT | TCG | AGT | TTG | TCT | AAG | GTT | GAG | CAT | GTG | GGA | GCA | 480 |
| Thr | Phe | Glu | Gln | Ala | Ser | Ser | Leu | Ser | Lys | Val | Glu | His | Val | Gly | Ala | |
| 145 | | | | | 150 | | | | | 155 | | | | | 160 | |
| GTG | ACC | AAG | GTT | TCA | GAT | CAA | AAA | AAT | CCA | GAA | CCA | GAT | GAA | TTG | GTG | 528 |
| Val | Thr | Lys | Val | Ser | Asp | Gln | Lys | Asn | Pro | Glu | Pro | Asp | Glu | Leu | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| GAT | ATT | CAA | ACC | CAC | TTT | AAT | CAT | AAA | TTG | CCG | ACT | GTA | TTG | TTT | GTT | 576 |
| Asp | Ile | Gln | Thr | His | Phe | Asn | His | Lys | Leu | Pro | Thr | Val | Leu | Phe | Val | |
| | | | 180 | | | | | 185 | | | | | 190 | | | |
| GGC | GGT | TCT | GCA | GGT | GCT | CGT | GTC | TTT | AAC | CAA | TTG | GTG | ACA | GAC | CAT | 624 |
| Gly | Gly | Ser | Ala | Gly | Ala | Arg | Val | Phe | Asn | Gln | Leu | Val | Thr | Asp | His | |
| | | 195 | | | | | 200 | | | | | 205 | | | | |
| AAG | AAA | GAA | CTA | ACA | GAG | CGC | TAC | AAT | ATT | ATC | AAT | CTA | ACT | GGA | GAT | 672 |
| Lys | Lys | Glu | Leu | Thr | Glu | Arg | Tyr | Asn | Ile | Ile | Asn | Leu | Thr | Gly | Asp | |
| | 210 | | | | | 215 | | | | | 220 | | | | | |
| TCT | AGT | CTG | AAC | GAG | TTG | AGC | CAA | AAT | CTT | TTT | CGT | GTT | GAC | TAT | GTG | 720 |
| Ser | Ser | Leu | Asn | Glu | Leu | Ser | Gln | Asn | Leu | Phe | Arg | Val | Asp | Tyr | Val | |
| 225 | | | | | 230 | | | | | 235 | | | | | 240 | |
| ACC | GAT | CTC | TAT | CAA | CCC | TTG | ATG | GAA | TTG | GCT | GAT | GTT | GTT | GTG | ACA | 768 |
| Thr | Asp | Leu | Tyr | Gln | Pro | Leu | Met | Glu | Leu | Ala | Asp | Val | Val | Val | Thr | |
| | | | | 245 | | | | | 250 | | | | | 255 | | |
| CGA | GGT | GGT | GCC | AAT | ACG | ATT | TTT | GAG | CTC | TTG | GCG | ATA | GCA | AAA | TTG | 816 |
| Arg | Gly | Gly | Ala | Asn | Thr | Ile | Phe | Glu | Leu | Leu | Ala | Ile | Ala | Lys | Leu | |
| | | | 260 | | | | | 265 | | | | | 270 | | | |
| CAT | GTC | ATT | GTG | CCG | CTT | GGT | CGT | GAA | GCT | AGT | CGT | GGT | GAC | CAG | ATT | 864 |
| His | Val | Ile | Val | Pro | Leu | Gly | Arg | Glu | Ala | Ser | Arg | Gly | Asp | Gln | Ile | |
| | | 275 | | | | | 280 | | | | | 285 | | | | |
| GAA | AAT | GCA | GCT | TAC | TTT | GTA | AAA | AAA | GGC | TAT | GCA | GAA | GAC | CTT | CAA | 912 |
| Glu | Asn | Ala | Ala | Tyr | Phe | Val | Lys | Lys | Gly | Tyr | Ala | Glu | Asp | Leu | Gln | |
| | 290 | | | | | 295 | | | | | 300 | | | | | |
| GAA | AGC | GAT | TTG | ACC | TTG | GAT | AGT | TTG | GAA | GAG | AAG | CTT | TCT | CAC | TTA | 960 |
| Glu | Ser | Asp | Leu | Thr | Leu | Asp | Ser | Leu | Glu | Glu | Lys | Leu | Ser | His | Leu | |
| 305 | | | | | 310 | | | | | 315 | | | | | 320 | |
| CTA | AGT | CAC | AAG | GAA | GAT | TAC | CAA | GCT | AAG | ATG | AAA | GCT | TCT | AAG | GAA | 1008 |
| Leu | Ser | His | Lys | Glu | Asp | Tyr | Gln | Ala | Lys | Met | Lys | Ala | Ser | Lys | Glu | |
| | | | | 325 | | | | | 330 | | | | | 335 | | |
| TTG | AAA | TCT | CTA | GCA | GAT | TTT | TAT | CAA | TTG | TTG | AAA | AAA | GAT | TTA | TCA | 1056 |
| Leu | Lys | Ser | Leu | Ala | Asp | Phe | Tyr | Gln | Leu | Leu | Lys | Lys | Asp | Leu | Ser | |
| | | | 340 | | | | | 345 | | | | | 350 | | | |
| TAA | | | | | | | | | | | | | | | | 1059 |
| * | | | | | | | | | | | | | | | | |

(2) INFORMATION FOR SEQ ID NO:2:

(i) SEQUENCE CHARACTERISTICS:
        (A) LENGTH: 352 amino acids
        (B) TYPE: amino acid
        (D) TOPOLOGY: linear     (ii) MOLECULE TYPE: protein     (xi) SEQUENCE DESCRIPTION: SEQ ID NO:2:

| | | | | | | | | | | | | | | |
|---|---|---|---|---|---|---|---|---|---|---|---|---|---|---|
| Met | Lys | Lys | Ile | Val | Phe | Thr | Gly | Gly | Gly | Thr | Val | Gly | His | Val | Thr |
| 1 | | | | 5 | | | | | 10 | | | | | 15 | |
| Leu | Asn | Leu | Leu | Leu | Met | Pro | Lys | Phe | Ile | Glu | Asp | Gly | Trp | Glu | Val |
| | | | 20 | | | | | 25 | | | | | 30 | | |
| His | Tyr | Ile | Gly | Asp | Lys | Arg | Gly | Ile | Glu | His | Gln | Glu | Ile | Leu | Lys |
| | | 35 | | | | | 40 | | | | | 45 | | | |
| Ser | Gly | Leu | Asp | Val | Thr | Phe | His | Ser | Ile | Ala | Thr | Gly | Lys | Leu | Arg |
| | 50 | | | | | 55 | | | | | 60 | | | | |
| Arg | Tyr | Phe | Ser | Trp | Gln | Asn | Met | Leu | Asp | Val | Phe | Lys | Val | Gly | Trp |
| 65 | | | | | 70 | | | | | 75 | | | | | 80 |
| Gly | Ile | Val | Gln | Ser | Leu | Phe | Ile | Met | Leu | Arg | Leu | Arg | Pro | Gln | Thr |
| | | | | 85 | | | | | 90 | | | | | 95 | |
| Leu | Phe | Ser | Lys | Gly | Gly | Phe | Val | Ser | Val | Pro | Pro | Val | Ile | Ala | Ala |
| | | | 100 | | | | | 105 | | | | | 110 | | |

```
Arg  Val  Ser  Gly  Val  Pro  Val  Phe  Ile  His  Glu  Ser  Asp  Leu  Ser  Met
          115                 120                      125
Gly  Leu  Ala  Asn  Lys  Ile  Ala  Tyr  Lys  Phe  Ala  Thr  Lys  Met  Tyr  Ser
     130                 135                      140
Thr  Phe  Glu  Gln  Ala  Ser  Ser  Leu  Ser  Lys  Val  Glu  His  Val  Gly  Ala
145                      150                 155                           160
Val  Thr  Lys  Val  Ser  Asp  Gln  Lys  Asn  Pro  Glu  Pro  Asp  Glu  Leu  Val
               165                      170                 175
Asp  Ile  Gln  Thr  His  Phe  Asn  His  Lys  Leu  Pro  Thr  Val  Leu  Phe  Val
               180                      185                      190
Gly  Gly  Ser  Ala  Gly  Ala  Arg  Val  Phe  Asn  Gln  Leu  Val  Thr  Asp  His
          195                      200                      205
Lys  Lys  Glu  Leu  Thr  Glu  Arg  Tyr  Asn  Ile  Ile  Asn  Leu  Thr  Gly  Asp
     210                      215                      220
Ser  Ser  Leu  Asn  Glu  Leu  Ser  Gln  Asn  Leu  Phe  Arg  Val  Asp  Tyr  Val
225                      230                      235                      240
Thr  Asp  Leu  Tyr  Gln  Pro  Leu  Met  Glu  Leu  Ala  Asp  Val  Val  Val  Thr
               245                      250                      255
Arg  Gly  Gly  Ala  Asn  Thr  Ile  Phe  Glu  Leu  Leu  Ala  Ile  Ala  Lys  Leu
          260                      265                      270
His  Val  Ile  Val  Pro  Leu  Gly  Arg  Glu  Ala  Ser  Arg  Gly  Asp  Gln  Ile
          275                      280                      285
Glu  Asn  Ala  Ala  Tyr  Phe  Val  Lys  Lys  Gly  Tyr  Ala  Glu  Asp  Leu  Gln
     290                      295                      300
Glu  Ser  Asp  Leu  Thr  Leu  Asp  Ser  Leu  Glu  Glu  Lys  Leu  Ser  His  Leu
305                      310                      315                      320
Leu  Ser  His  Lys  Glu  Asp  Tyr  Gln  Ala  Lys  Met  Lys  Ala  Ser  Lys  Glu
                    325                      330                      335
Leu  Lys  Ser  Leu  Ala  Asp  Phe  Tyr  Gln  Leu  Leu  Lys  Lys  Asp  Leu  Ser
               340                      345                      350
```

( 2 ) INFORMATION FOR SEQ ID NO:3:

( i ) SEQUENCE CHARACTERISTICS:
    ( A ) LENGTH: 1059 base pairs
    ( B ) TYPE: nucleic acid
    ( C ) STRANDEDNESS: single
    ( D ) TOPOLOGY: linear   ( i i ) MOLECULE TYPE: mRNA   ( i i i ) HYPOTHETICAL: NO   ( i v ) ANTI-SENSE: NO   ( x i ) SEQUENCE DESCRIPTION: SEQ ID NO:3:

```
AUGAAAAAAA  UUGUCUUUAC  AGGUGGGGGG  ACGGUUGGAC  ACGUUACCCU  CAAUCUUUUG      60
UUAAUGCCCA  AGUUCAUCGA  AGAUGGUUGG  GAAGUCCACU  AUAUCGGGGA  CAAGCGUGGU     120
AUCGAACACC  AAGAAAUCCU  UAAGUCAGGU  UGGAUGUCA   CUUCCACUC   CAUUGCGACU     180
GGGAAAUUGC  GUCGCUAUUU  CUCUUGGCAA  AAUAUGCUGG  ACGUCUUCAA  AGUUGGCUGG     240
GGAAUCGUCC  AAUCGCUCUU  UAUCAUGUUG  CGACUUCGUC  CACAGACCCU  UUUUUCAAAG     300
GGGGGCUUUG  UCUCAGUACC  GCCUGUUAUC  GCAGCGCGUG  UGUCAGGAGU  GCCUGUCUUU     360
AUUCACGAAU  CUGACCUGUC  UAUGGGCUUG  GCCAAUAAAA  UCGCCUAUAA  AUUUGCGACU     420
AAGAUGUAUU  CAACCUUUGA  GCAAGCUUCG  AGUUUGUCUA  AGGUUGAGCA  UGUGGGAGCA     480
GUGACCAAGG  UUUCAGAUCA  AAAAAAUCCA  GAACCAGAUG  AAUUGGUGGA  UAUUCAAACC     540
```

-continued

| | | | | | |
|---|---|---|---|---|---|
| CACUUUAAUC | AUAAAUUGCC | GACUGUAUUG | UUUGUUGGCG | GUUCUGCAGG | UGCUCGUGUC | 600
| UUUAACCAAU | UGGUGACAGA | CCAUAAGAAA | GAACUAACAG | AGCGCUACAA | UAUUAUCAAU | 660
| CUAACUGGAG | AUUCUAGUCU | GAACGAGUUG | AGCCAAAAUC | UUUUUCGUGU | UGACUAUGUG | 720
| ACCGAUCUCU | AUCAACCCUU | GAUGGAAUUG | GCUGAUGUUG | UUGUGACACG | AGGUGGUGCC | 780
| AAUACGAUUU | UUGAGCUCUU | GGCGAUAGCA | AAAUUGCAUG | UCAUUGUGCC | GCUUGGUCGU | 840
| GAAGCUAGUC | GUGGUGACCA | GAUUGAAAAU | GCAGCUUACU | UUGUAAAAAA | AGGCUAUGCA | 900
| GAAGACCUUC | AAGAAAGCGA | UUUGACCUUG | GAUAGUUUGG | AAGAGAAGCU | UUCUCACUUA | 960
| CUAAGUCACA | AGGAAGAUUA | CCAAGCUAAG | AUGAAAGCUU | CUAAGGAAUU | GAAAUCUCUA | 1020
| GCAGAUUUUU | AUCAAUUGUU | GAAAAAAGAU | UUAUCAUAA | | | 1059